United States Patent [19]

Barer

[11] 4,057,643

[45] Nov. 8, 1977

[54] ANTIFUNGAL COMPOSITIONS OF BUTANEDIOL BIS (CHLOROACETATE)

[75] Inventor: Sol J. Barer, Clark, N.J.

[73] Assignee: Celanese Corporation, New York, N.Y.

[21] Appl. No.: 666,801

[22] Filed: Mar. 15, 1976

[51] Int. Cl.$^2$ .............................................. A01N 9/24
[52] U.S. Cl. .................................................. 424/311
[58] Field of Search ........................................ 424/311

[56] References Cited

U.S. PATENT DOCUMENTS

| | | | |
|---|---|---|---|
| 1,816,441 | 7/1931 | Peet | 424/311 |
| 2,446,505 | 8/1948 | Arenson | 424/311 |
| 2,627,489 | 2/1953 | Drake et al. | 424/27 |
| 3,427,388 | 2/1969 | Scoggin | 424/273 |

OTHER PUBLICATIONS

Nerdel et al., C. A. vol. 50, (1956), 15429g.
Fusco et al., C. A. vol. 45, (1951), 549f.

*Primary Examiner*—Allen J. Robinson

[57] ABSTRACT

Antifungal compositions incorporating 1,4-butanediol bis(chloroacetate), and methods for combatting fungal infestation, especially in agriculture.

4 Claims, No Drawings

ANTIFUNGAL COMPOSITIONS OF BUTANEDIOL BIS (CHLOROACETATE)

This invention is concerned with new and useful antifungal compositions and particularly with such compositions containing 1,4-butanediol bis (chloroacetate) as the antifungal agent.

Antifungal agents are well known in agriculture and their use if specifically for control of fungus infection of plants, and in particular valuable crop plants such as tomato, rice, wheat and the like. Various classes of chemical compounds are known to have antifungal activity and include esters of diols wherein the esterifying acid is acetic acid and haloacetic acids, especially chloroacetic acids. Thus, U.S. Pat. No. 1,816,441 describes the antifungal activity of such compounds as ethylene glycol bis(chloroacetate) and trimethylene glycol bis(chloroacetate), i.e., ethanediol bis(chloroacetate) and 1,3-propanediol bis(chloroacetate), respectively. Glycol mono- and diesters formed with fatty acids as the esterifying acid are described in U.S. Pat. No. 2,446,505 as mold inhibitors, and in U.S. Pat. No. 2,627,489 as insect repellants. Ethylene glycol bis(trichloroacetate) is a known commercial herbicide.

It has now been found that 1,4 butanediol bis (monochloroacetate) has surprisingly higher order of antifungal activity than the corresponding known diesters of ethylene glycol and 1,3-propanediol and are also of significant activity against fungi which are substantially unaffected by the said known diesters at the usual levels of concentration commonly employed.

1,4-Butanediol bis(monochloroacetate) is a known compound and is prepared by art recognized techniques, e.g., by acylation of the butanediol with monochloroacetyl chloride or monochloroacetic anhydride.

When directly compared with ethylene glycol bis(monochloroacetate), 1,2-propanediol bis(monochloroacetate) and even 1,3-butanediol bis(monochloroacetate), 1,4 butanediol bis(monochloroacetate) shows remarkably higher activity against certain fungi, e.g., those responsible for late blight of tomatoes and leaf rust of wheat, against which the former are effective, and shows substantial activity against fungus responsible for rice blast disease against which the former are not effective at the levels tested.

Even at lower than normal concentration levels, 1,4-butanediol bis(monochloroacetate) has substantial activity against fungi, the activity being higher than that attainable with either ethyleneglycol, 1,3-butanediol or 1,2-propanediol bis(monochloroacetate) at normal concentration levels. For example, at 1200 ppm, ethylene glycol bis(monochloroacetate) shows 63% control of leaf rust of wheat while 1,4-butanediol bis(monochloroacetate) shows 84% control at a level of only 300 ppm. Thus, by employing the present antifungal agents at substantially lower levels, it is possible to attain control of fungi at least comparable to that attainable with much higher levels of the ethylene glycol diester.

Notwithstanding the higher antifungal activity, the present antifungal agents are also characterized by little or no injury to plant substrates at normal concentration levels.

In addition to their use in agriculture, the antifungal compositions of this invention can also be used in the prevention of mold growth on non-agricultural substrates, such as textile fibers, leather and the like.

DESCRIPTION OF PREFERRED EMBODIMENTS

The antifungal compositions of this invention are formulated by dissolution of the antifungal agent in an appropriate solvent therefor to form concentrates which are suitable for dilution with water to produce spraying compositions. Appropriate solvents include various organic solvents, but preferably water-soluble organic solvents such as lower alkanols, e.g., methyl and ethyl alcohol; ketones, such as acetone; dioxane; tetrahydrofuran and similar such water-soluble solvents, as well as mixtures thereof. Water-soluble solvents are usually preferred since the foliar spray utilizes water as the extending agent. However, water-insoluble solvents such as naphtha, kerosene, petroleum ether and similar such solvents can also be employed. In all cases, it is preferred to employ wetting agents and surfactants to ensure uniform distribution of the antifungal agent in the spray produced with the solvent concentrates.

As an alternative, the antifungal agent can be suspended in water with the aid of surfactants and wetting agents and the resulting mixture used for spraying, either directly or as a concentrate for use with additional water as extending agent.

The concentration of antifungal agent in the agricultural spray can vary depending on the substrate, the type and extent of fungus infection, the method of spray application, the plant sites, and other factors familiar to those skilled in the art. Usually, concentrates containing fixed amounts of antifungal agent are employed with varying amounts of the extending agent, i.e., water, to obtain sprays containing varying concentrations of the active agent. For most purposes, the concentration of active agent in the aqueous spray is sufficient to provide from about ½ to about 4 pounds of antifungal agent per acre. The efficiency of the method of spray application will, of course, dictate the concentration of antifungal agent required. With the usual spray application methods, the spray should contain from about 600 to about 4800 parts per million of active agent for effective fungus control and preferably from about 1200 to about 4800 ppm for best results.

Of the butanediol bis(chloroacetates), it is surprising that the 1,4-isomer has much greater activity than the 1,3-isomer. The latter shows insignificant activity against leaf rust of wheat or late blight of tomatoes whereas the 1,4-isomer is of very high order of effectiveness. When tested against various fungi for effectiveness of control, the 1,4-derivative shows substantial activity against a variety of fungi, and the activity is substantially of high order as compared to similar known antifungal agents such as the corresponding deschloro esters, e.g., butanediol diacetates, as well as ethanediol and propanediol bis(chloroacetates). Further, at the levels tested, the present new compounds show substantial activity against certain fungi against which the aforesaid related compounds show little or no activity. In view of the comparative testing, the present antifungal agent is not only of greater activity than corresponding deschloro esters or lower alkanediol bis(chloroacetates) against certain fungi but also has a broader spectrum of antifungal activity.

As with any agricultural compositions, the present new compounds may also contain other biologically active materials, including other agricultural agents, e.g., bactericides, other fungicides, nematocides, insecticides, fertilizer, fruit-thinning agents, and the like; surfactants and other additives such as corrosion inhibitors, antifoaming agents, sticking agents and extending agents commonly employed in such compositions. The surfactants used are surface-active agents which are acceptable for agricultural use. These are well-known in the art and are described in the patent literature, e.g., see U.S. Pat. No. 3,427,388.

As mentioned hereinbefore, it is preferred to provide concentrates of the compositions of this invention for eventual use in spraying applications. The concentrates are prepared at concentrations of the active ingredients to provide the required levels of antifungal agent for the intended purpose, i.e., as a spray for application to the substrate. Commonly, the concentrates are diluted with water and spray-applied using standard techniques and equipment.

The concentrates are preferably comprised of solutions of the antifungal agent in the selected solvent which may range in concentration from as little as about 0.05% to the saturation concentration of the agent in the selected solvent. Where the antifungal agent is of limited solubility, e.g., less than 1 or 2% by weight, any excess over the solubility can be provided by merely suspending the agent in the solvent. In the latter instance, in particular, and preferably in all concentrates, a surfactant or dispersing agent may be incorporated into the concentrate to maximize uniform dispersion of the antifungal agent in water when the concentrate is used for spray applications. Most commonly, the amount of antifungal agent in the concentrate will range from about 0.05 to as much as about 10% by weight based on the weight of solvent, and preferably from about 2 to about 5% by weight. The concentrates may contain water or other diluents. Large quantities of water are usually avoided since the presence of water is not required and water can be added to the concentrate as needed when used in spray application, but small quantities of water, e.g., 1-2% by volume, can be present.

The concentrates are diluted with water to provide the spray concentrations required in actual application. The dilution can be accomplished by aspiration of the concentrate into a stream or spray of water using known aspirator-type spray apparatus, or alternatively by direct dilution with water to specified concentrations after which the diluted concentrate is then spray-applied using known pressure-spray applicators. Accordingly, a concentrate comprising 0.05% by weight antifungal agent in a solvent on dilution with water at a ratio of 20:1 provides a spray composition in which the antifungal agent is at 25 ppm, while a 1% solution on the same dilution would provide a spray composition in which the insecticide is at 500 ppm. Thus, by selecting suitable concentrates of known concentrations, a spray composition of any desired concentration of insecticide and diol can be produced.

The following examples are provided to further illustrate the invention.

EXAMPLE I

The following test procedures are used in evaluation of the fungicides of this invention as foliar protectants.

For all test procedures, candidate compounds are dissolved in a suitable solvent (acetone, methyl alcohol or ethyl alcohol) and diluted to desired concentration with deionized water containing wetting and dispersing agents to obtain spray solutions.

A. Heterobusidiomycetes is a class of fungi containing many agriculturally important pathogens. Leaf Rust of wheat, *Puccinia recondita* var. *tritici* (LRW) is used as a test organism to represent this class.

Wheat plants, *Triticum vulgare,* approximately seven to eight days old and four to five inches tall are mounted on a compound turntable and sprayed at 40 pounds pressure for 60 seconds with respective candidate compounds at concentrations indicated.

After drying, treated plants are dusted with spores of *Puccinia recondita* var. *tritici* directly from diseased plants and then immediately placed in an incubation chamber maintained at 70° F and 95% plus relative humidity. After the proper incubation period, plants are removed to the greenhouse for disease development.

Disease severity (infection pressure) is determined by actual count of development pustules on inoculated but otherwise untreated controls. Control effectiveness is determined by actual count of the number of developed pustules appearing on the respective treatments compared directly to equivalent developed pustules developing on inoculated but otherwise untreated controls. All units of test include a minimum of three replicates.

B. Ascomycetes is a class of fungi containing many agriculturally important pathogens. Powdery mildew of cucumbers, *Erysiphe cichoracearum,* (PMC) is used in these experiments as a representative of this fungal class.

Straight-eight cucumber (*Cumcumis sativas*) plants in first true leaf stage, approximately 14 to 18 days old, grown under greenhouse conditions are mounted on a compound turntable and sprayed to incipient run-off at 30 psi with candidate compound at concentration indicated, using 30ml of the spray solution per five relicates (equivalent to approximately 200 gpa).

After treated plants have dried, they are placed among diseased (*Erysiphe cichoracearum*) cucumber plants, subjected to an initial spore shower by dusting with spores from diseased plants nd then left undisturbed in place for approximately ten days. By this procedure treated plants are subjected to the cited initial spore shower as well as to continuing natural infection pressure from surrounding inoculum. Observations ten days after intial inoculation determine effectiveness of treatments. Untreated controls will generally reflect 75 to 100% leaf area diseased at this time. Effectiveness of treatment is determined by direct comparison of the average percentage leaf area infection on treated plants with the average percentage leaf area infection on untreated inoculated control.

C. Phycomycetes is a class of fungi containing plant pathogens of agricultural importance. Late blight of tomato, *Phytophthora infestans,* (LBT), is used in these experiments as a representative of this fungal class.

Bonny Best tomato plants, *Lycopersicon esculentum,* approximately 5 to 6 weeks old, in five-leaf growth stage, are mounted on a compound turntable and sprayed at 30 pounds pressure with the candidate compound at concentration indicated.

After drying, treated plants are spray-inoculated with a mixed sporangial and zoospore suspension of *Phytophthora infestans* and immediately placed in an incubation chamber maintained at 70° F and 95% plus relative humidity. After 40 hours in the incubation chamber, plants are removed and observed for total infection lesions of the top three leaves. Effectiveness of treatments is determined by direct comparison with inoculated controls. All units of test include a minimum of three replicates.

D. RICE BLAST DISEASE, *Piricularia oryzae*, (RBD)

Rice plants in fully developed second-leaf stage are mounted on a compound turntable and sprayed to incipient run-off at 30 psi with the candidate compound at concentrations indicated using 30ml of the spray solution per three (3) replicates (equivalent to approximately 200 gpa).

After drying, treated plants are spray-inoculated at 30 pounds pressure with an equeous spore suspension of *Piricularia oryzae* and then immediately placed in an incubation chamber maintained at 70° F and 95% plus RH. After proper incubation time, plants are removed to the green house for disease development. Infection lesions are sufficiently developed within 5 days after inoculation to permit assessment of control. Disease severity is determined by actual count of the number of infection lesions developing on untreated inoculated controls. Effectiveness of treatment is determined by direct comparison of the number of infection lesions appearing on the respective treated plants compared directly with those lesions appearing on untreated inoculated controls. All units of test include a minimum of three replicates.

E. BACTERIAL LEAF SPOT OF TOMATOES, *Xanthomonas vesicatoria* (BLST)

Bonny Best tomato plants approximately 6 to 7 weeks old, in six to seven leaf growth stage, are mounted on a compound turntable and sprayed at 30 psi with candidate compound at concentrations indicated.

After drying, treated plants are spray-inoculated at 30 pounds pressure with an equeous cell suspension of *Xanthomonas vesicatoria* containing 5% Carborundum and then immediately placed in an incubation chamber maintained at 70° F and 95% plus RH. After 40 hours in the incubation chamber, plants are removed to the green house for further development of infection lesions. Disease severity is determined by count of lesions present on six to seven treated leaves. Effectiveness of treatment is determined by direct comparison with inoculated controls.

The results obtained with 1,4-butanediol bis(chloroacetate) compared with 1,3-butanediol diacetate and 1,4-butanediol diacetate are given in Table I.

The 0–10 Phytotoxicity scale measures the relative injury observed on the plants following application of the tested chemicals. "0" indicates no injury; 1, a trace; 2–3, slight injury with no reduction in growth; 4–6, some reduced growth associated with injury; 7–9, severe injury from which plants do not recover; 10, plants are dead.

TABLE I

| Test Material | ppm | Percent Control:Plant Injury (0–10 scale) | | | | |
| --- | --- | --- | --- | --- | --- | --- |
| | | LRW | PMC | LBT | RBD | BLST |
| 1,3-butanediol diacetate | 1200 | 0:0 | 0:0 | 0:0 | 0:0 | 0:0 |
| 1,4-butanediol diacetate | 1200 | 0:0 | 0:0 | 2:0 | 0:0 | 0:0 |
| 1,4-butanediol bis(chloroacetate) | 1200 | 100:0 | 27:0 | 99:0 | 47:0 | 0:0 |
| Inoculated Controls(1) | | 74.3 | 91.6 | 293 | 70.3 | 59 |

(1)Inoculated controls, each based on average of 3 replicates, expressed as infection loci per plant for LRW, LBT, RBD and BLST and percent leaf area diseased for PMC.

EXAMPLE 2

The test procedures of Example 1 are repeated, excepting the BLST test, using 1,3 and 1,4-butanediol bis (chloroacetate). For comparison, ethylene glycol bis(chloroacetate) and 1,2-propanediol bis(chloroacetate) are similarly tested and the results given in Table II.

TABLE II

| COMPOUND | Percent Control: Plant Injury (0–10) | | | | |
| --- | --- | --- | --- | --- | --- |
| | Level (ppm) | LRW | PMC | LBT | RBD |
| Ethylene glycol bis(monochloracetate) | 1200 | 63:0 | 0:0 | 67:1 | 0:10 |
| 1,2-propanediol bis(monochloracetate) | 1200 | 10:0 | 31:0 | 40:0 | 0:0 |
| 1,3-Butanediol bis(monochloracetate) | 1200 | 13:0 | 33:0 | 0:0 | 16:0 |
| 1,4-Butanediol bis(monochloracetate) | 1200 | 100:0 | 27:0 | 99:0 | 47:0 |
| 1,4-Butanediol bis(monochloracetate) | 600 | 88:0 | — | 92:0 | — |
| 1,4-Butanediol bis(monochloracetate) | 300 | 84:0 | — | 62:0 | — |
| 1,4-Butanediol bis(monochloracetate) | 100 | 58:0 | — | 35:0 | — |

What is claimed is:

1. A method of combatting fungal infection on plants which comprises applying to said plants an antifungal effective amount of 1,4-butanediol bis(chloroacetate).

2. The method according to claim 1 wherein said butanediol bis(chloroacetate) is employed in the form of a foliar spray.

3. The method according to claim 2 wherein said butanediol bis(chloroacetate) is employed at a level of at least 1200 ppm in said spray.

4. The method according to claim 2 wherein said butanediol bis(chloroacetate) is employed at a level of from about 1200 ppm to about 4800 ppm in said spray.

* * * * *